US 6,723,103 B2

(12) United States Patent
Edwards

(10) Patent No.: US 6,723,103 B2
(45) Date of Patent: Apr. 20, 2004

(54) RONGEUR AND RONGEUR CLEANING METHOD

(76) Inventor: Elizabeth Ann Edwards, 301 Summit St., Lebanon, OH (US) 45036

( * ) Notice: Subject to any disclaimer, the term of this patent is extended or adjusted under 35 U.S.C. 154(b) by 0 days.

(21) Appl. No.: 10/236,219

(22) Filed: Sep. 6, 2002

(65) Prior Publication Data

US 2004/0049200 A1 Mar. 11, 2004

(51) Int. Cl.⁷ .............................................. A61B 17/00
(52) U.S. Cl. ........................................................ 606/83
(58) Field of Search ........................... 606/83, 61, 205; 433/4, 159, 160

(56) References Cited

U.S. PATENT DOCUMENTS

| | | | | |
|---|---|---|---|---|
| 315,706 A | * | 4/1885 | Brewer et al. ............... | 433/159 |
| 348,628 A | * | 9/1886 | Hewett ......................... | 433/39 |
| 388,619 A | * | 8/1888 | Booth ........................... | 433/39 |
| 1,143,927 A | * | 6/1915 | Allen ............................ | 433/144 |
| 1,299,102 A | * | 4/1919 | Angle ....................... | 235/70 D |
| 1,910,740 A | * | 5/1933 | Barsha .......................... | 433/38 |
| 5,273,519 A | * | 12/1993 | Koros et al. ................... | 606/83 |
| 5,286,255 A | * | 2/1994 | Weber ........................... | 604/22 |
| 5,484,441 A | * | 1/1996 | Koros et al. ................... | 606/79 |
| 5,569,258 A | * | 10/1996 | Gambale ...................... | 606/83 |
| 5,702,420 A | * | 12/1997 | Sterling et al. .............. | 606/205 |
| 5,947,279 A | * | 9/1999 | Lee et al. .................... | 206/232 |
| 6,085,411 A | * | 7/2000 | Stewart et al. ................ | 29/760 |
| 6,261,296 B1 | * | 7/2001 | Aebi et al. ..................... | 606/90 |
| 2001/0005786 A1 | * | 6/2001 | Michelson .................... | 606/83 |
| 2003/0069584 A1 | * | 4/2003 | Agbodoe ...................... | 606/83 |

* cited by examiner

Primary Examiner—Pedro Philogene
Assistant Examiner—David A Bonderer
(74) Attorney, Agent, or Firm—Stephen J. Stark; Miller & Martin PLLC

(57) ABSTRACT

A rongeur having a crossbar with a cutter and a shaft with a footplate. The crossbar moves towards the footplate through movement of an actuator connected to the crossbar about an arcuate path about a first pivot. This results in a portion of the crossbar moving initially away from the shaft as the cutter moves towards the footplate to create a gap, and then back towards the shaft as the cutter contacts the footplate.

A spring mechanism biases the crossbar in a ready position with a first distance separating the cutter and the footplate. When the cutter contacts the footplate, the crossbar is in a cutting position. When the crossbar is between the ready position and the cutting position, it is in an intermediate position with a gap between the crossbar and the shaft. A retainer is positioned in an engaged position to maintain the crossbar in an intermediate position for cleaning. The retainer is preferably a disposable O-ring which is disposed after each use. The retainer counteracts the bias of the spring mechanism while maintaining the gap.

13 Claims, 4 Drawing Sheets

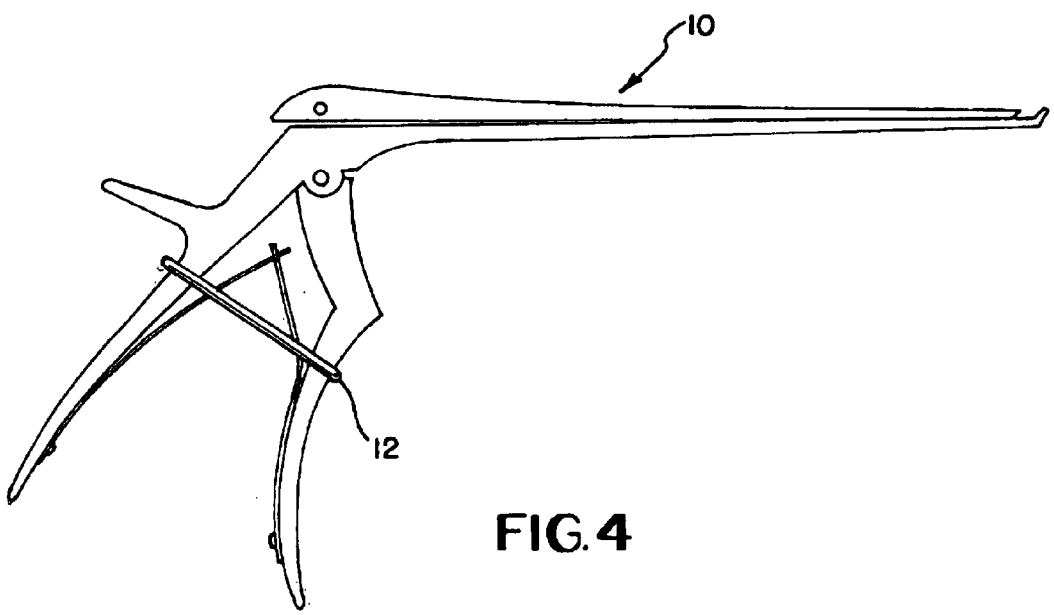
FIG. 4
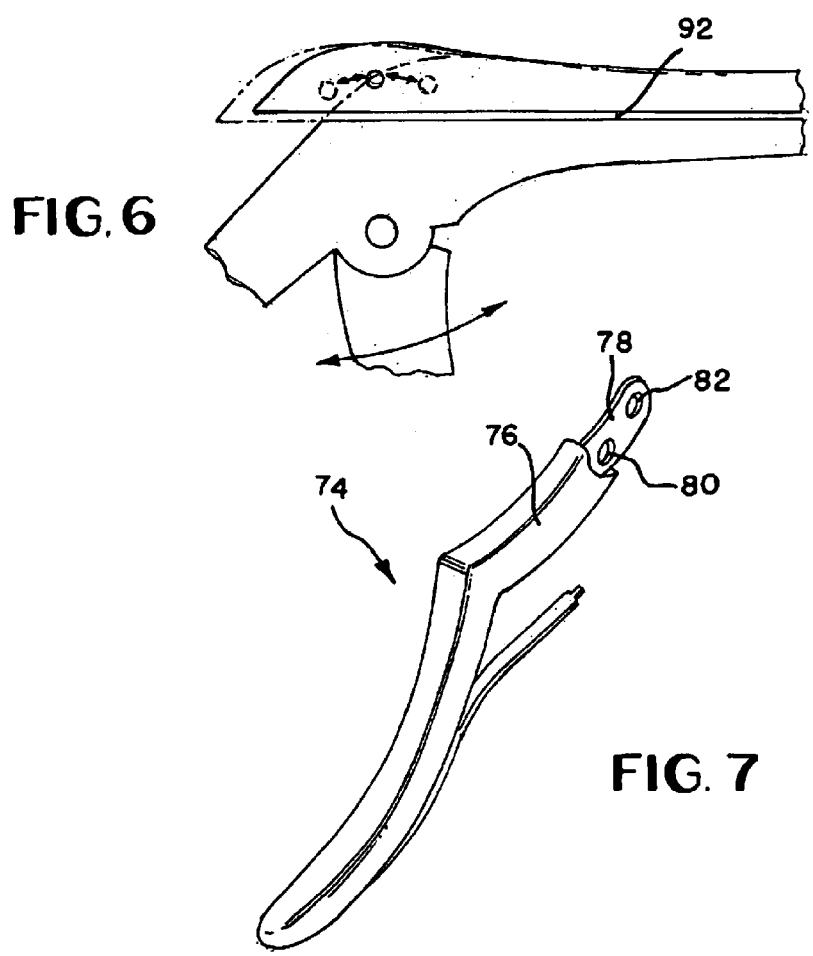
FIG. 6
FIG. 7

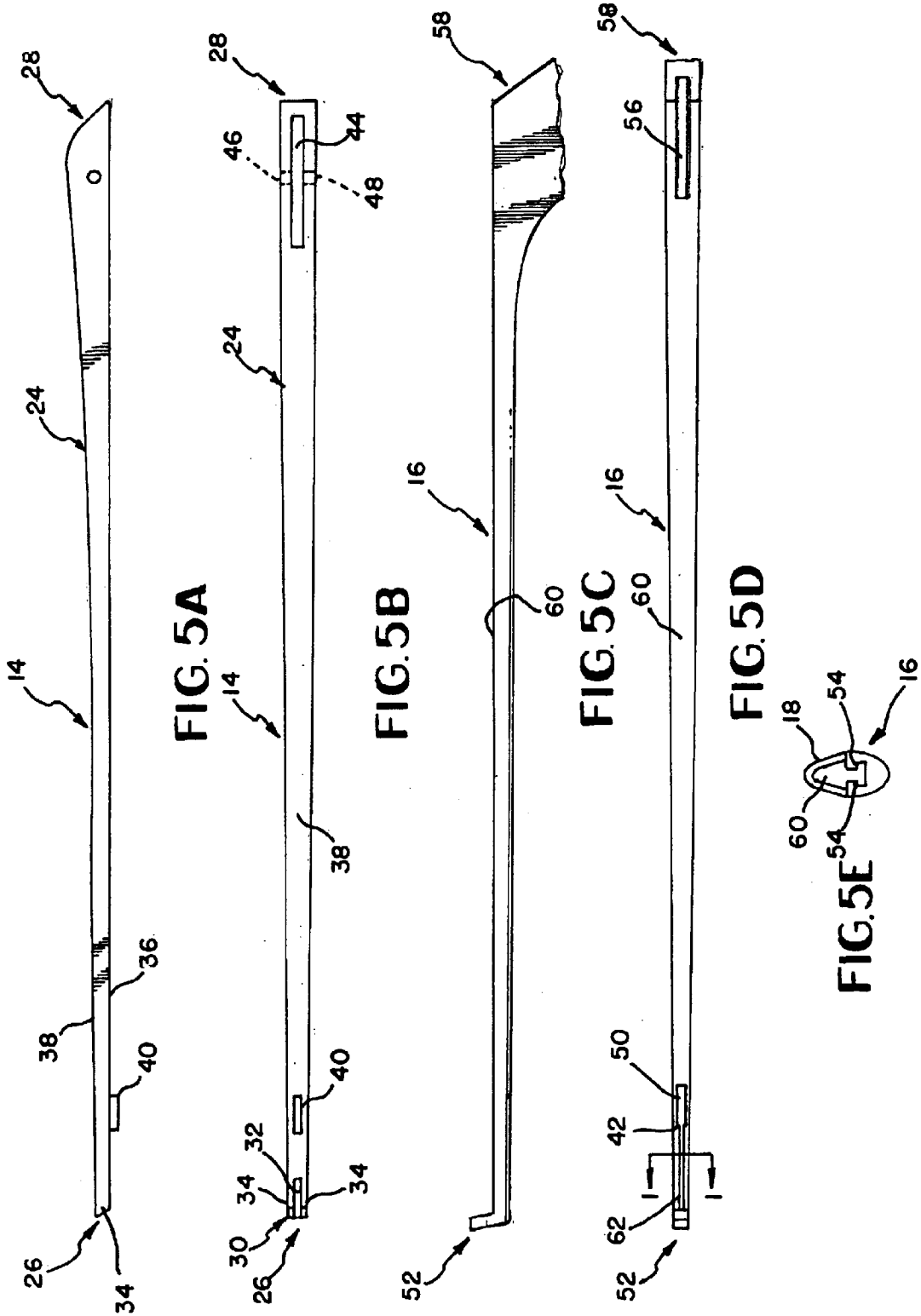

RONGEUR AND RONGEUR CLEANING METHOD

BACKGROUND OF THE INVENTION

The present invention relates to a specific medical device known as a rongeur, and more particularly to a rongeur and a method of cleaning a rongeur between uses.

The rongeur is a medical instrument utilized for a variety of specific tasks. It is particularly useful for removing small amounts of bone, although it is sometimes utilized to remove cartilage or other body material from such places as the knee, cervix, and vertebrae in the back, to name a few specific applications.

A rongeur normally has a long fixed shank with an anvil or a footplate at its distal end and a handle at its proximal end. A reciprocating shaft or crossbar moves substantially axially with respect to the fixed shank, either inside a hollow fixed shank or along the outside surface of a rigid fixed shank. An abutment forming a cutter on the distal end of the reciprocating crossbar abuts the footplate to cut tissue captured between the cutter and the footplate. The proximal end of the crossbar is attached to a trigger mechanism for the reciprocating of the crossbar to move the cutter against the footplate.

A traditional trigger mechanism is often utilized having a grip which is received along the palm of a user. The grip is usually not moveable with respect to the rigid fixed shaft. A lever rotates about a first pivot relative to the grip, with a first portion of the lever grasped by a user. A second portion of the lever is located between the first pivot and a second pivot which connects with the crossbar. A spring mechanism separates the first portion of the lever from the grip. Similar structures may be seen in U.S. Pat. Nos. 5,312,407 and 5,061,269.

To operate the trigger mechanism, a user grasps the trigger and squeezes the first portion toward the grip to overcome the bias of the spring mechanism. The first portion pivots toward the grip and the second portion rotates about the first pivot. As this occurs, the second pivot along with the crossbar are moved along the rigid fixed shaft until the cutter contacts the foot plate.

In most ronjeur designs, as the second portion of the lever rotates about the first pivot, it follows a circular path. This causes a portion of the crossbar, including the second pivot, near the proximal end of the rigid fixed shaft to move upwardly away from the rigid fixed shaft initially during the operation of the trigger mechanism. At a point during the operation process, a line through the first and second pivots would be perpendicular to the rigid fixed member and the second pivot will begin to move back towards the rigid fixed shaft as it moves the second pivot towards the distal end and the cutter towards the foot plate. Once the cutter contacts the footplate and applies a force, the crossbar may once again be contacting the rigid fixed shaft near the second pivot.

When the first portion of the lever is released, the spring mechanism applies a force to separate the first portion of the lever from the grip to draw the crossbar in the proximal direction. When the crossbar contacts the rigid fixed shaft near the second pivot, proximal, or rearward motion of the crossbar stops thereby leaving a space between the cutter and the footplate. This is a ready position for the rongeur.

While the movement of the crossbar at the second pivot upwardly and downwardly does not affect the ability of the cutter to operate with the footplate to a significant degree, it does create a gap during operation which allows for tissue, debris or body fluids including blood to enter the gap during operation.

Since the resting position of the rongeur is with the rigid fixed member in contact with the crossbar along their interfacing surfaces, any entrapped debris or solution between the interfacing surfaces may not be removed during the cleaning process. Accordingly, although a rongeur may be steam cleaned, since the entrapped waste is located between interfacing surfaces, it is not easily removed during the cleaning process.

Failure to remove entrapped waste could result in a build up resulting in the operation of the rongeur to be "sticky". This creates problems for the surgeon as well as for the surgical equipment manufacturer. A specific feel is anticipated by the surgeon during each use of the rongeur. Additionally, health risks may result to a subsequent patient since bacteria could cultivate on waste products. This poses a number of problems for the patient as well as the medical community.

A number of rongeurs and techniques have been developed to attempt to solve the problem of eliminating waste from interfacing surfaces of rongeurs. Some rongeurs are disassembled during the cleaning process. While this is a very good way of cleaning a rongeur, the re-assembly of the rongeur is sometimes challenging for personnel. Furthermore, if parts are inadvertently lost during the cleaning process, the rongeur will not operate properly. U.S. Pat. No. 5,961,531 describes various other problems with disassembling rongeurs for cleaning purposes and describes a "convertible" rongeur, apparently one which allows the crossbar to be lifted away from the rigid fixed shaft without requiring detachment, or removal, of any parts.

While U.S. Pat. No. 5,961,531 provides one way of addressing the problem of cleaning between the crossbar and the rigid fixed member, it creates a new level of complexity in the construction of a rongeur. A need still exists for a simpler, and less complicated rongeur and method of cleaning a rongeur while still preserving the utility of prior art rongeurs.

SUMMARY OF THE INVENTION

Consequently, it is an object of the present invention to provide a rongeur and a method of cleaning a rongeur that permits thorough cleaning without disassembly of the rongeur.

It is another object of the present invention to provide a rongeur which is not partially disassembled during the cleaning process.

Another object of the present invention is to provide a method for cleaning a rongeur which adequately removes entrapped waste between the crossbar and the rigid fixed shaft.

Accordingly, the present invention provides a rongeur with a crossbar which moves relative to a rigid fixed shaft having a footplate at a distal end. A distal end of the crossbar operates as a cutter with footplate of the rigid fixed shaft. The crossbar is operably coupled to an actuator proximal to the distal end. The actuator pivots about a first pivot.

The first pivot separates the lever into a first and a second portion. As the lever is operated to move the crossbar so that the cutter contacts the footplate, the second portion, or actuator, moves along a circular path about the first pivot. This lifts the crossbar away from the rigid fixed shaft where the crossbar is operated by the second portion of the lever to create a gap. Once the operating point and the first pivot are aligned perpendicularly to the rigid fixed shaft, the second portion then directs the operating point towards the rigid fixed member along the circular path as the cutter nears the footplate to close the gap between the crossbar and the rigid fixed shaft at the operating point. While similar structure is utilized in the prior art, no one is believed to have undertaken efforts to clean the rongeur while maintaining a gap between the crossbar and the rigid fixed.

Accordingly a releasable, removable, and preferably a disposable retainer is utilized to maintain the gap between the crossbar and the rigid fixed shaft during the cleaning operation by positioning the retainer to partially operate the crossbar between the ready and the cutting position with the gap being maintained between the crossbar and the rigid fixed shaft. The retainer may take the form of a disposable O-ring which overcomes at least some of the bias of the spring member which normally would maintain the rongeur in a ready position.

BRIEF DESCRIPTION OF THE DRAWINGS

The particular features and advantages of the invention as well as other objects will become apparent from the following description taken in connection with the accompanying drawings in which:

FIG. 4 is a side plan view of the rongeur of FIG. 1 with the retainer in location for cleaning;

FIG. 5A is a side plan view of a crossbar of the rongeur of FIG. 2;

FIG. 5B is a top plan view of the crossbar of FIG. 5A;

FIG. 5C is a side plan view of a rigid fixed member of the rongeur of FIG. 2;

FIG. 5D is a top plan view of the rigid fixed member of FIG. 5C;

FIG. 5E is a cross sectional view taken along the line 1—1 of FIG. 5D;

FIG. 6 is a detailed view of the gap created during the operation of the rongeur; and FIG. 7 is a top plan view of the lever used in the rogeur of FIG. 2.

DESCRIPTION OF THE PREFERRED EMBODIMENT

Figure 1:
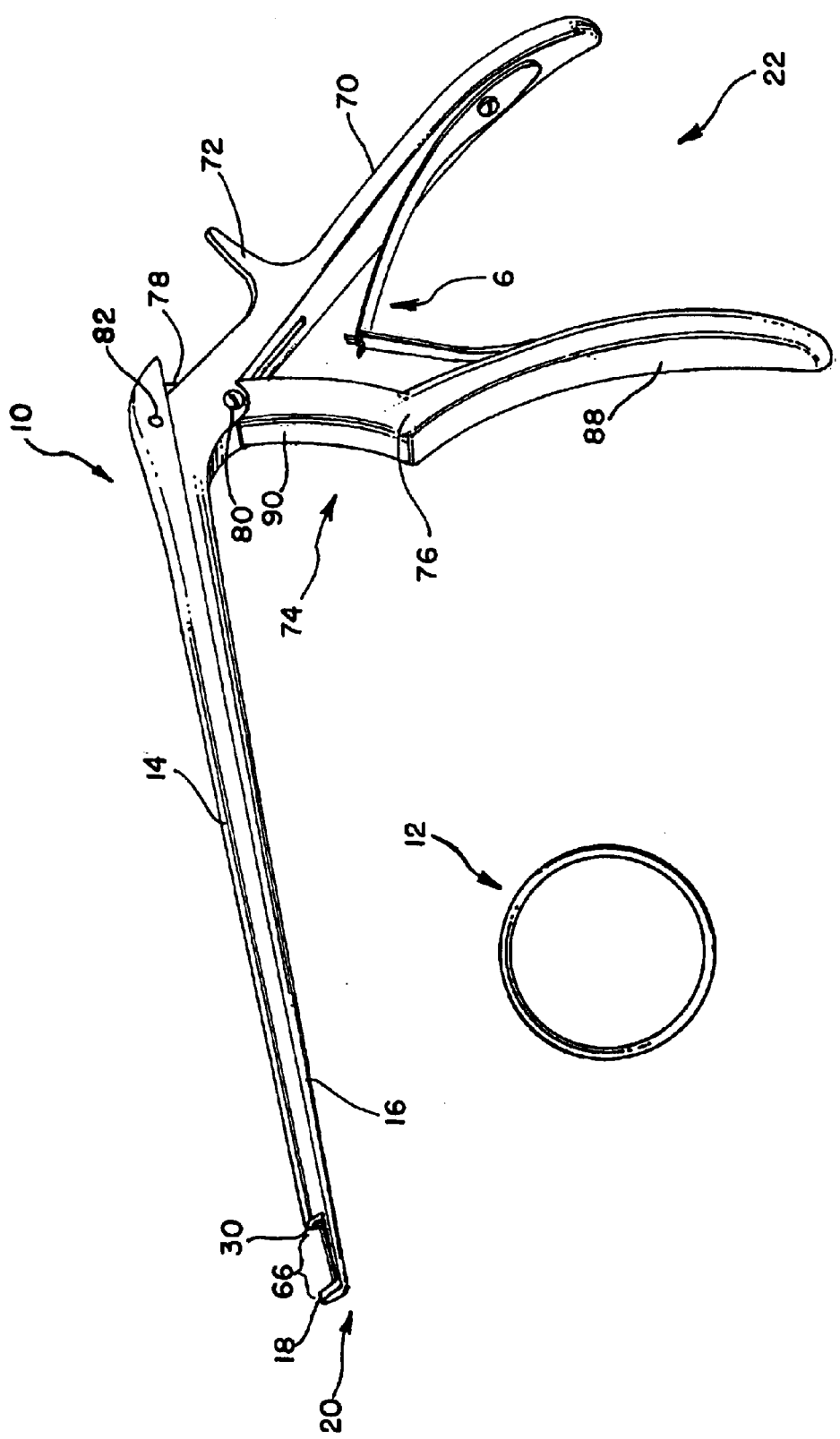
FIG. 1 is a side elevational view showing a rongeur in a ready position with a retainer of the preferred embodiment.
Figure 2:
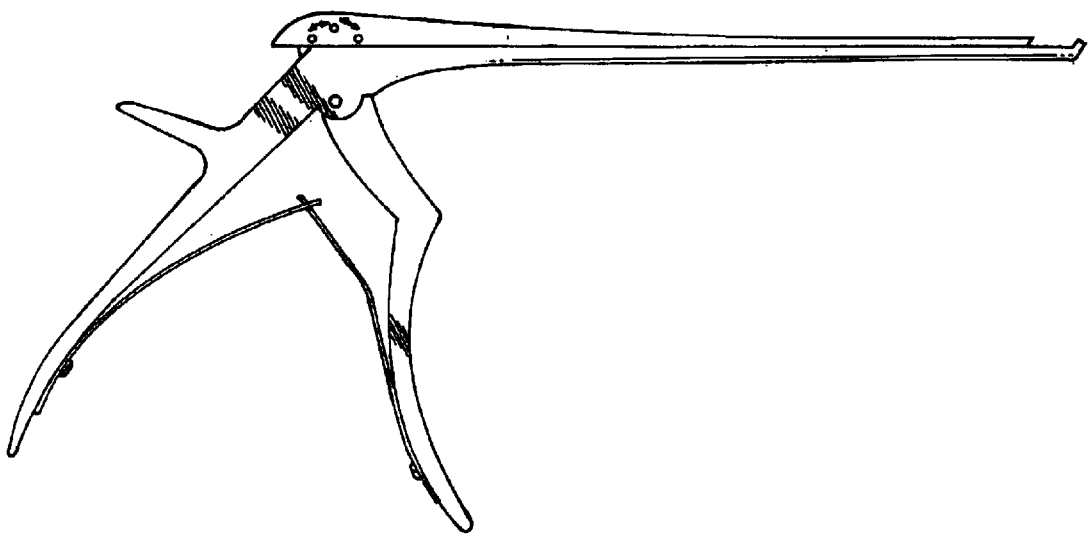
FIG. 2 is a side plan view of a rongeur in an intermediate position between the ready position and a cutting position.
Figure 3:
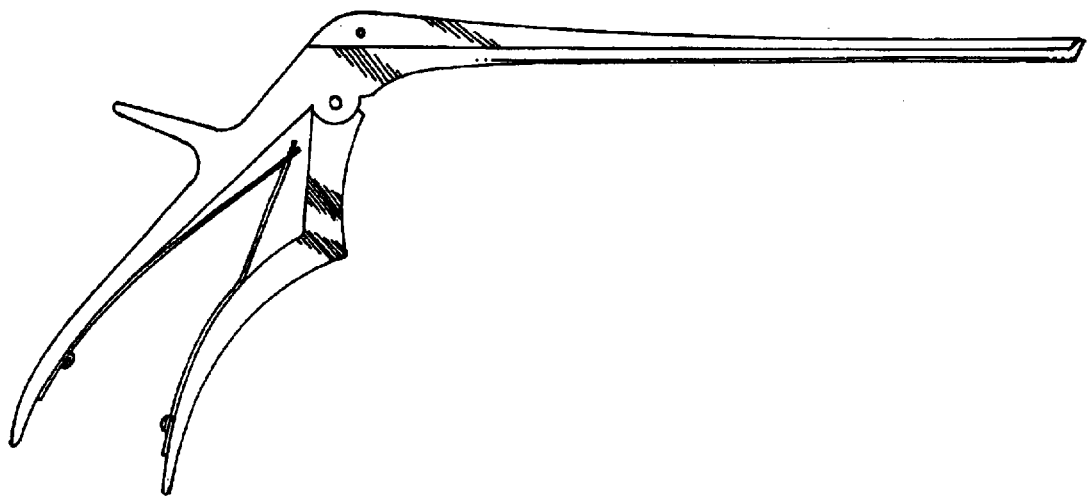
FIG. 3 is a side plan view of the rongeur of FIG. 2 in the cutting position.

FIG. 1 shows a ronjeur 10 along with a retainer 12. The retainer 12 is preferably detachable from the rongeur 10 and disposable as illustrated.

The rongeur 10 is shown in a ready position in FIG. 1 with a crossbar 14 in a fully retracted position as will be explained in detail below. The crossbar is moveable relative to a rigid fixed shaft 16 which has a footplate 18 at the distal end 20. A trigger mechanism 22 moves the crossbar 14. Detail of the crossbar 14 and shaft 16 may be seen in FIGS. 5A–5E detached from one another.

The crossbar 14 is illustrated as a shank 24 having a distal end 26 and a proximal end 28. The shank 24 has a blade 30 at the distal end 26. The blade 30 has a chamber 32 located between edges 34. The chamber 32 may retain material cut with the rongeur 10. The crossbar 14 also has an interfacing surface 36 and an opposed surface 38. A director 40 is either formed in or extends from the interfacing surface 36. The director 40 cooperates with a receiver 42 of the shaft 16 as will be explained in further detail below.

The crossbar 14 also includes a slot 44 which receives an actuator (not shown in FIGS. 5A–5E), which connects with the crossbar 14, usually at or near the distal end 28 of the crossbar. A pin (not shown in FIGS. 5A–5E) is received in bores 46,48 and retained therein with the actuator at least partially located within slot 44.

The shaft 16 with footplate 18 has a receiver 42 which cooperates with the director 40. The director 40 is placed within opening 50 and then slid toward the distal end 52 of the shaft 16. The director 40 cooperates with the ledges 54 to be retained within the receiver 42 during operation of the rongeur 10. The director 40 and receiver 42 cooperate to substantially eliminate lateral movement of the crossbar 14 during operation.

The shaft 16 includes a duct 56 at the proximal end 58 of the shaft 16. The duct 56 provides a passage for the actuator (not shown in FIGS. 5A–5E) to be received therethrough to connect with the crossbar 14. The shaft 16 has an interfacing side 60 which cooperates with the interfacing side 38 of the crossbar 14.

The footplate 18 of the shaft 16 includes a recess 62 which may also retain severed material during operation of the rongeur 10 and assist in the cutting action with the blade 30 of the crossbar 14.

FIGS. 1 and 7 are useful in illustrating the trigger mechanism 22. The trigger mechanism has a handle, or grip 70 which is fixedly connected to the shaft 16. The grip 70 receives the palm portion of a user. A spur 72 may assist in locating the user's hand on the grip 70. A lever 74 is moveable relative to the grip 70. The lever 74 is comprised of a first portion 76 and a second portion 78 which are separated by a first pivot 80 where the lever 74 rotates relative to the grip 70. A second pivot 82 is located on the second portion 78 and serves as the actuator in conjunction with pin 68 to move the crossbar 14 distally from the ready position to a cutting position.

FIGS. 1–3 and 6 are useful in showing the normal operation of the rongeur 10. FIG. 1 shows the rongeur 10 in a ready position. The trigger mechanism 22 is biased by the spring mechanism 64 which preferably comprises first and second spring members 84,86 to cause the crossbar 14 to be fully retracted proximally away from the footplate 18 in the ready position. The interfacing sides 36,60 of crossbar 14 and shaft 16 contact one another along a large portion of the surface of area of each of the interfacing sides 36,60. The separation between the blade 30 and footplate 18 creates a mouth 66 which is fully open in the ready position. The crossbar cannot move further in the proximal direction as it is constrained mechanically by a pin 68 along with the director 40, the receiver 42 and the interfacing sides 36,60.

In order to move the crossbar 14 to a cutting position, the user squeezes the first portion 76 of the lever 74 toward the grip 70. The first portion 76 may be divided into first and second curved surfaces 88,90 for comfort of the user. As the fist portion 76 of the lever 74 is squeezed, the bias of the spring mechanism is overcome and the first portion 76 rotates toward the grip 70 thereby rotating the second portion 88 away from the grip 70. This moves the second pivot 82 arcuately about the first pivot 80.

FIG. 6 shows the movement of the proximal end 28 of the crossbar 14 during the cutting process. As the lever 74 is moved, the actuator, or second pivot 82, moves in an arcuate manner. Initially, in addition to moving toward the distal end of the shaft 16, the crossbar also moves upwardly to create gap 92. Once the first and second pivots 80,82 are aligned perpendicularly to the shaft 16, a maximum amount of gap 92 is created, then as the lever 74 is further pulled, the crossbar 14 moves back toward the shaft 16 as it moves distally to the cutting position shown in FIG. 3 where the blade 30 is contacting the footplate 18. In between the cutting position illustrated in FIG. 3 and the ready position shown in FIG. 1, the rongeur is in an intermediate position with a gap 92 created between the crossbar 14 and the shaft 16.

When in use, the rongeur 10 may receive waste in the form of tissue, debris, or fluids, including blood within the gap 92. If the rongeur were to be cleaned according to traditional methods, it would remain in the ready position, with the interfacing surfaces 36,60 contacting one another, and there is a strong likelihood that some waste would remain between the interfacing surfaces after the cleaning process. Cleaning may include steam cleaning at temperature with steam, mechanical brush cleaning and/or ultrasound cleaning techniques. Even sterilization may not result in removal of entrapped waste between the interfacing surfaces 36,60.

FIG. 4 shows the retainer 12 of the preferred embodiment in operation. The retainer 12 may take the form of an o-ring made of an approved material. As shown in FIG. 1, the o-ring is preferably removable from the rongeur 10 so that it does not interrupt the normal operation of the rongeur 10, or disrupt the feel of the device when in use by a surgeon. It is anticipated that the o-ring be disposable so that it has a single use. A plurality of retainers 12 may be supplied with or separately from the rongeur 10.

The retainer 12 may be placed on the rongeur 10 by squeezing the trigger mechanism 22 to the cutting position. If the retainer 12 has resilient portions, it may deflect some during the application of the retainer 12 about the grip 70 and lever 74. The retainer 12 is then placed in a desired location, and the trigger mechanism 22 is released to maintain the crossbar in an intermediate position with the gap 92 created between the crossbar 14 and the shaft 16. The bias of the spring member 64 maintains the intermediate position of the rongeur 10 and the retainer 12 prevents the trigger mechanism 22 from returning the crossbar 14 to the ready position.

In the preferred embodiment, the gap 92 is near its maximum, with the first and second pivots aligned perpendicularly to the interfacing surface 60 of the shaft 16 when the retainer 92 is placed in the installed position.

When the retainer 12 is installed on the trigger mechanism 22 to the preferred engaged position, it is located so that it contacts the grip 70 just below the spur 72 and the first portion 76 of the lever 74 along the first curved surface 88 near where the first and second curved surfaces 88,90 meet at knee 94. Other installed or spacing could include further down the first curved portion 88 and further below the spur 72 on the grip 70. Alternatively, the retainer 12 may be positioned on the grip 70 above the spur 72 and on the first curved surface 88.

The rongeur 10, with the retainer 12 in the desired installed position, is then processed through the cleaning process. A brush or other appropriate tool may be utilized to remove waste through mechanical cleaning. Next the rongeur 10, with the retainer 12 installed, may be subjected to an ultrasonic cleaning process. This step is much more effective with the gap 92 between the interfacing surfaces 36,60 as the interfacing surfaces 36,60 has been a problematic location for waste build up.

When the retainer 12 has resilient portions, or is formed of a resilient material such as the ultrasonic action of this cleaning step may result in the flexing and retraction of the retainer 12 during this process. This may assist in dislodging waste caught between the director 40 and the receiver 42, however, the gap 92 will cause an angle between surfaces in the receiver 42 and director 40, and resiliency of the retainer 12 is not required in all embodiments.

The rongeur 10, with the retainer 12 in the installed position, may also be cleaned with solution or steam, such as are often utilized in various sterilization techniques. Normally steam is elevated to over 250 degrees Farenheit, such as between about 250 to 275 degrees for a specific period of time. The separation of the interfacing surfaces 36,60 during this process allows for a more thorough cleaning of the rongeur 10 than has been done in the prior art.

Although the retainer 12 is illustrated as a disposable o-ring in the preferred embodiment, more complicated retainers could be developed which are permanently attached to a portion of the rongeur 10. Other retainer designs could be positioned within the gap 92 instead of directly contacting one or more portions of the trigger mechanism 22.

The functional capability of the retainer 12 is to position the crossbar 14 relative to the shaft 16 to expose at least a portion of the interfacing surfaces 36,60 during at least a portion of the cleaning process without requiring a user to continually apply pressure to the trigger mechanism 22 and tie up a hand which may be needed for other tasks during cleaning or may not be accessible, such as when the rongeur 10 is being subjected to steam cleaning.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A rongeur comprising:

a fixed shaft having an interfacing surface and a distal end with a footplate;

a crossbar having an interfacing surface and a distal end with an abutment, said crossbar operably coupled relative to the shaft to contact and retract the abutment relative to the footplate;

an actuator rotatable through an arc about a first pivot, said actuator connected to the crossbar distally from the abutment at a connection point;

a spring member normally biasing the crossbar in a ready position with the abutment a first distance from the footplate;

a trigger mechanism operably coupled to the actuator configured to rotate the actuator about the first pivot moving the abutment towards the footplate when operated while rotating the actuator about the first pivot moving the connection point in an arc from the ready position distally towards the footplate and initially away from the interfacing side of the shaft to create a gap between the interfacing surfaces of the shaft and crossbar in an intermediate position, and upon contact of the footplate and the abutment, said rongeur being in a cutting position; and a resilient retainer having an engaged position and a disengaged position, wherein when in said engaged position said retainer maintains the crossbar at least proximate to an intermediate position while allowing at least limited flexing and contracting of the retainer, and when in said disengaged position, said retainer does not interfere with operation of the rongeur.

2. The rongeur of claim 1 wherein said abutment is a cutter.

3. The rongeur of claim 1 wherein interfacing surface of the shaft is planar, and said engaged position of said retainer locates said connection point relative to said shaft so that a line through said connection point and said first pivot is substantially perpendicular to said interfacing surface of said shaft.

4. A rongeur comprising:

a fixed shaft having an interfacing surface and a distal end with a footplate;

a crossbar having an interfacing surface and a distal end with an abutment, said crossbar operably coupled relative to the shaft to contact and retract the abutment relative to the footplate;

an actuator rotatable through an arc about a first pivot, said actuator connected to the crossbar distally from the abutment at a connection point;

a spring member normally biasing the crossbar in a ready position with the abutment a first distance from the footplate;

a trigger mechanism operably coupled to the actuator configured to rotate the actuator about the first pivot moving the abutment towards the footplate when operated while rotating the actuator about the first pivot moving the connection point in an arc from the ready position distally towards the footplate and initially away from the interfacing side of the shaft to create a gap between the interfacing surfaces of the shaft and crossbar in an intermediate position, and upon contact of the footplate and the abutment, said rongeur being in a cutting position; and a retainer having an engaged position and a disengaged position, wherein when in said engaged position said retainer maintains the crossbar in an intermediate position, and when in said disengaged position, said retainer does not interfere with operation of the rongeur, and wherein when said retainer is in said disengaged position, said retainer does not contact the rongeur.

5. The rongeur of claim 4 wherein the retainer is disposable.

6. The rongeur of claim 4 wherein the retainer is an O-ring.

7. The rongeur of claim 4 wherein the retainer acts on the trigger mechanism in the engaged position.

8. The rongeur of claim 7 wherein the retainer is an O-ring.

9. The rongeur of claim 8 wherein the o-ring is resilient.

10. The rongeur of claim 7 wherein the trigger mechanism further comprises a grip and a lever, and the retainer is placed relative to the grip and the lever in the engaged position.

11. The rongeur of claim 10 wherein the lever further comprises first and second curved portions connected at a knee, said grip further comprises a spur extending therefrom, and the retainer is located between the first curved surface and the grip below the spur.

12. The rongeur of claim 4 wherein said abutment is a cutter.

13. The rongeur of claim 4 wherein interfacing surface of the shaft is planar, and said engaged position of said retainer locates said connection point relative to said shaft so that a line through said connection point and said first pivot is substantially perpendicular to said interfacing surface of said shaft.

* * * * *